United States Patent [19]

Randen

[11] Patent Number: 4,816,256

[45] Date of Patent: Mar. 28, 1989

[54] MOSQUITO REPELLENT COMPOSITIONS

[75] Inventor: Neil A. Randen, Stillwater, Minn.

[73] Assignee: Minnesota Mining and Manufacturing Company, St. Paul, Minn.

[21] Appl. No.: 917,482

[22] Filed: Oct. 10, 1986

[51] Int. Cl.$^4$ .............................................. A61K 27/12
[52] U.S. Cl. ..................... 424/405; 424/407; 424/487; 424/DIG. 10
[58] Field of Search ........ 424/405, 407, 487, DIG. 10

[56] References Cited

U.S. PATENT DOCUMENTS

| | | | |
|---|---|---|---|
| 3,576,760 | 4/1971 | Gould et al. | 424/487 X |
| 3,590,118 | 6/1971 | Conrady | 424/19 |
| 3,966,902 | 6/1976 | Chromecek | 424/487 X |
| 4,172,122 | 10/1979 | Kubik et al. | 424/59 |
| 4,303,675 | 12/1981 | Di Pietro et al. | 424/343 |
| 4,304,591 | 12/1981 | Mueller et al. | 71/93 |
| 4,335,104 | 6/1982 | Van Cleave | 424/59 |
| 4,477,467 | 10/1984 | Nishizawa et al. | 424/317 |
| 4,552,755 | 11/1985 | Randen | 424/81 |

FOREIGN PATENT DOCUMENTS 0231001 12/1984 Japan .................................. 424/407

OTHER PUBLICATIONS

"Polymer Handbook", (edited by Bandrup and Immergut, pp. IV, 344–358.

Primary Examiner—Nancy A. B. Swisher
Attorney, Agent, or Firm—Donald M. Sell; Walter N. Kirn; Carolyn A. Bates

[57] ABSTRACT

Mosquito repellent compositions comprising an active agent and an oil-soluble, water insoluble acrylate polymer having specific solubility parameters of approximately 6–10 (cal/cc)$^{\frac{1}{2}}$ in poorly hydrogen bonding solvents are disclosed. The compositions are substantive to the skin, have increased effective lifetimes and are cosmetically acceptable.

9 Claims, No Drawings

MOSQUITO REPELLENT COMPOSITIONS

BACKGROUND OF THE INVENTION

The present invention relates to mosquito repellent compositions comprising an active agent and an oil-soluble, water insoluble acrylate polymer. The compositions are more substantive to human skin and are thus more effective than prior insect repellent compositions.

Over the years, chemical agents such as dimethyl phthalate and N,N-diethyl-m-toluamide (DEET) have been applied to the human skin as insect repellents. They function by vaporizing from the skin. Initially, when there is a large reservoir, evaporation is rapid, which depletes the reservoir and quickly reduces the effectiveness. In addition, the agents can be absorbed directly into the body, rubbed off or washed off by perspiration or water, again depleting the reservoir. In hot and humid weather, the active agent loses its effectiveness even faster. In order to solve these problems, solvents and other chemicals have been incorporated into formulations to improve their effective lifetimes.

U.S. Pat. No. 3,590,118 describes a composition which incorporates known chemical repellents and a water soluble terpolymer resin in a solution which forms a film when applied to skin. The repellent is slowly released to the environment by diffusion and the composition has an effective life longer than that of the repellent agent alone. Effectiveness of up to 24 hours in a temperate climate has been observed. However, the film is stiff which can result in flaking of the film and loss of repellent qualities.

U.S. Pat. No. 4,477,467 describes an insect repellent composition containing DEET as the active agent and an aromatic proton donor as carrier. The carrier can be: (a) monocyclic aromatic with substituted hydroxyl or carbonyl groups or both; and (b) polycyclic aromatic with substituted hydroxyl or carbonyl groups or both. This repellent composition is said to have a longer lasting effect due to increased resistance to absorption through the skin by forming a complex.

U.S. Pat. No. 3,966,902 describes a composition comprising an effective amount of an active ingredient such as a medicinal agent, a disinfectant, a pesticide, an insect repellent or a cosmetic agent in a carrier polymer of a monomer having hydrophilic functional groups containing aluminum, zinc or zirconium bound in complex form. The monomers can be hydroxyl alkyl esters of alpha-beta-unsaturated carboxylic acids (2-hydroxyethylacrylate or methacrylate). These monomers can be reacted with aluminum salts to form complexes.

U.S. Pat. No. 4,304,591 describes a water-insoluble hydrophilic gel comprising a hydrophilic polymer of mono-olefinic monomers cross-linked with a major amount of a diolefinic non-hydrophilic monomer for use as a carrier for medicaments, pesticides, and fragrances for controlled release.

U.S. Pat. No. 4,335,104 describes a multi-purpose anhydrous cosmetic composition which comprises a water insoluble surfactant in combination with active chemical agents. The product has increased and/or prolonged activity in topical applications to skin.

U.S. Pat. No. 4,303,675 describes a mosquito repellent which has a persistent action and is water soluble. The active agent consists of 2,5-dimethyl-2,5-hexanediol and is formulated with an inert carrier in the form of a cream, lotion, spray, soaking agents for towels or a thermal diffusion tabloid.

SUMMARY OF THE INVENTION

The present invention relates to mosquito repellent compositions which are cosmetically acceptable and effective in-vivo over long periods of time. The compositions comprise an active agent and an oil-soluble, water insoluble acrylate polymer which is compatible with the active agent. These polymers have specific solubility parameters of approximately 6–10 $(cal/cc)^{\frac{1}{2}}$ in poorly hydrogen bonding solvents.

DETAILED DESCRIPTION OF THE INVENTION

The mosquito repellent compositions of the present invention comprise an active ingredient and an oil soluble, water insoluble acrylate polymer.

The acrylate polymers which are useful in the present invention are those which have been described in U.S. Pat. No. 4,552,755, which patent is incorporated herein by reference, and include homopolymers, copolymers, terpolymers, etc., derived from the polymerization of at least one ester monomer of Formula I:

Formula I wherein
$R^1$ is an alkyl radical containing 4 to 18 carbon atoms in cyclic, straight or branched-chain configuration, and
$R^2$ is hydrogen or lower alkyl.

The term "lower alkyl" refers to an alkyl radical containing one to four carbon atoms.

The polymer may optionally contain up to 30 mole percent of the same or different monomers of Formula II below:

Formula II wherein $R^3$ is H or an alkyl group containing 1 to 18 carbon atoms; $R^4$ is hydrogen, methyl, or $-CO_2R^3$, and $R^5$ is hydrogen, lower alkyl or $-CH_2CO_2R^3$; provided when $R^4$ is not hydrogen, $R^5$ is hydrogen and when $R^5$ is not hydrogen, $R^4$ is hydrogen. When difunctional acid monomers only are included along with an ester monomer of Formula I, the mole percent of such acid monomers should not exceed about 15 in order to maintain the required solubility parameters. The acrylate polymers must be present in the formulation above a certain threshold amount for effective evaporation control.

The preferred acrylates are those which are compatible with the active agents and which generally have solubility parameters of 6–10 $(cal/cc)^{\frac{1}{2}}$ in poorly hydrogen bonding solvents.

The acrylate polymers used in the compositions can be prepared from the corresponding alkyl esters of acrylic acid, methacrylic acid, etc., wherein the ester alkyl groups may contain 4 to 18 carbon atoms and are exemplified by butyl, iso-amyl, octadecyl, stearyl groups and the like. Esters wherein the alkyl group contain less than four carbon atoms may be included in small amounts, e.g., less than 10 mole percent. However, in order to achieve the requisite solubility parameters, and polymers should generally not contain a significant amount of lower alkyl ester monomers.

The acrylate polymers may optionally contain up to 30 mole percent of the unesterfied $\alpha,\beta$-olefinically unsaturated carboxylic acids of Formula II such as acrylic acid or methacrylic acid provided the resulting polymer exhibits the requisite solubility parameter. The presence of the carboxylic acid monomer increases the removability of the compositions with soap and water.

The preferred acrylate polymers are derived from 0 to 20 mole percent of the acid monomers and from 80 to 100 mole percent of the alkyl ester monomers. Especially preferred monomers are:

n-butyl acrylate, n-butyl methacrylate, iso-butyl acrylate, iso-butyl methacrylate, sec-butyl acrylate, sec-butyl methacrylate, n-amyl acrylate, n-amyl methacrylate, iso-amyl acrylate, iso-amyl methacrylate, n-hexyl acrylate, n-hexyl methacrylate, cyclohexyl acrylate, 2-ethylbutyl acrylate, 2-ethylbutyl methacrylate, n-heptyl acrylate, n-heptyl methacrylate, n-octyl acrylate, n-octyl methacrylate, 2-ethylhexyl acrylate, 2-ethylhexyl methacrylate, iso-octyl acrylate, n-nonyl acrylate, n-nonyl methacrylate, n-decyl acrylate, n-decyl methacrylate, iso-decyl acrylate, iso-decyl methacrylate, undecyl methacrylate, lauryl acrylate, lauryl methacrylate, hexadecyl acrylate, hexadecyl methacrylate, octadecyl acrylate, octadecyl methacrylate, stearyl methacrylate, acrylic acid, methacrylic acid, ethacrylic acid, maleic acid, itaconic acid, $\beta$-carboxyethyl acrylate.

The preparation of the polymers from the olefinically unsaturated monomers is well documented in the literature and can be carried out by standard bulk, solution or emulsion techniques. Generally, the latter two are preferred with solution polymerization being most preferred. The polymerization of the monomers is catalyzed by free radical-generating catalysts such as peroxides, azo catalysts and the like. To be most effective, the reactor for such polymerization should be purged with an inert gas in order to remove traces of oxygen. The solution polymerizations are run in a compatible solvent and the final polymer solution preferably contains 25 to 60 percent solids.

The molecular weight of the acrylate polymers used in the compositions may vary over a broad range. The molecular weight must be suitably large to provide the requisite binding effect. The upper limit is determined only by formulation requirements. As the molecular weight increases, the polymers tend to become too viscous to formulate easily into cosmetically appealing compositions. Generally, polymers having a Brookfield viscosity between 50 and 250,000 cps, and preferably between 200 and 25,000 cps when measured at 25 percent novolatiles, will be useful in the compositions of the invention.

The acrylate polymers useful in the compositions are insoluble in water and must have a solubility parameter between about 6–10 $(cal/cc)^{\frac{1}{2}}$ in poorly hydrogen-bonding solvents. The method for determining solubility parameter ranges of polymers and an extensive list of solvents (classified as either poorly hydrogen-bonding, moderately hydrogen-bonding, or strongly hydrogen-bonding) are described in "*Polymer Handbook*" (edited by Bandrup and Immergut), pages IV, 344–358. Acrylate polymers having the requisite solubility parameters are oil-soluble and compatible with the active agents.

For effective control of the rate of vaporization of active agents, the acrylate polymers must be present in the formulation above a threshold weight percent. This threshold differs for different types of active ingredients. The molecular weight of the acrylate polymers is also an important consideration and the preferred molecular weight varies with the active agent.

U.S. Pat. No. 4,552,755 teaches that the incorporation of specific oil soluble, water insoluble acrylate polymers into oil-in-water emulsion formulations will result in an improved moisturizing composition by maintaining the emollient oils on the skin's surface longer. Therefore, it was quite surprising when a slightly different oil—the mosquito repellent N,N-diethyl-m-toluamide (DEET), when formulated with such oil soluble, water insoluble acrylate polymers was found to still evaporate at an appreciable rate. Completely contrary to what was expected, the evaporation rate of the DEET was hardly suppressed. In fact, it was very similar to that of native DEET at the same concentration. However, what was more surprising was the fact that even though the evaporation rates of DEET from these formulations were very similar initially, the formulations containing the acrylate polymer apparently still had an evaporation rate high enough to effectively repel mosquitoes later on.

6 HOUR SUBSTANTIVITY TEST

The effectiveness of any formulation is measured according to the following test:

The in-vivo substantivity of a composition is determined 6 hours after application by quantifying the amount of applied active agent still present on a test site. Basically, the method consists of applying an active agent to a participant's forearm and extracting the site 6 hours later. The extracted solutions are analyzed on a gas chromatograph to determine the amount of active agent present on said site. This can be compared to the theoretical amount applied and the percent retention calculated—the higher the percent retention, the more substantive the composition.

The steps used in carrying out the substantivity test are as follows:

1. The outside portion of the participant's lower arm (below the elbow), is washed with Ivory soap by passing lathered hands up and down the arm five times. The soap is rinsed with tap water and the arm is patted dry with a clean cloth or paper towel.
2. The participant is asked to sit in a chair with his/her arm resting on a table. The palm of the hand faces downwardly and the elbow is bent at a 90° angle.
3. Using a 6×12 cm template, a rectangular test site is marked via a series of dots with a nonpermanent ink pen on the broadest portion of the subject's outer forearm.
4. A minimal grease barrier (Apiezon N, Apiezon Products Ltd., London) $\frac{1}{8}$ inch wide is carefully placed around the marked test site to prevent spreading of the test composition.
5. A 200 $\mu$l aliquot of the test composition is applied to the lower half of the test site and spread evenly and thoroughly over the 6×6 cm area with a needleless syringe. Another 200 $\mu$l aliquot of the same test composition is applied in the same manner to the upper half of the 6×12 cm area.

6. The control composition is applied to the other arm in the same manner.
7. The participant is allowed to go about his/her daily activities, taking care not to brush the test sites.
8. Six hours after the application, the participant is asked to come back to have the test sites extracted.
9. Each test site is extracted at two locations with the participant's arm in the same position as in Step 1. One end of a hollow glass cylinder 25 mm long and having an inside diameter of 40 mm, is lubricated with a thin layer of Apiezon N grease to prevent solvent leakage. This end of the cylinder is pressed onto the lower portion of the test site by the subject. Ten (10.0) ml of methyl ethyl ketone (MEK) is poured into the cylinder on the test site. The MEK is agitated by using a 10 ml needleless glass syringe to withdraw and discharge the solvent in the glass cylinder. The force of the discharge solvent is directed at different locations each time. After eleven (11) such cycles, the MEK is removed completely and placed in a container which is tightly capped. The glass cylinder is carefully removed so as not to allow any residual solvent to run into the other half of the test site. The extracted side is wiped dry with a tissue and then the upper site extracted with fresh MEK as above.
10. When the glass cylinder is pressed firmly against the arm to prevent solvent leakage, the underlying tissue puckers up into the center of said cylinder. To relieve this stress, the skin appears to stretch, and it stretches more in one direction than in the other. When the cylinder is removed, an elliptical identation remains on the skin surface showing exactly where the test site was extracted. To determine the extracted area, the inner major and minor axes of the elliptical indentation are measured in hundredths of a centimeter. These diameters are recorded for future calculations.
11. The test site is wiped with a heptane saturated paper towel to remove the Apiezon grease barrier and any residual DEET. The arms are then washed with soap and water and dried.

A Hewlett Packard 5880A gas chromatograph, equipped with Level Four Temperature Programming, Integrator and Methods, an automatic sampler and a 25 meters×0.3 mm ID SE-54 silicone capillary column is used to analyze the samples. The following procedure is employed.

1. Three DEET standard samples containing approximately 0.0300 g, 0.0150 g, and 0.0050 g, respectively, are weighed out. Approximately 50 g of methyl ethyl ketone are added to solubilize each sample, and the resulting solution is weighed to a tenth of a milligram. The percent DEET for each of these standard solutions is calculated.
2. The DEET standards are analyzed on the gas chromatograph using conditions which give reasonable retention times for DEET. This will vary depending on column used, temperatures used, flow rates, etc.
3. A calibration table is set up on the gas chromatograph by dividing the calculated percent DEET in the standard solutions by their respective chromatographic integrated area.
4. The extraction samples obtained in Step 9 above are also run on the chromatograph. The chromatograph will print out the percent DEET in the extraction samples by comparing their areas to the stored calibration table. From this, the percent DEET retention on the participants can be calculated.

CALCULATIONS

The percent retention of the DEET for each sample formulation is calculated using the following formula:

$$\text{Percent Retention} = 2.82744(10)^7 \frac{\mu l - g - cm^2}{ml} \times \frac{(\% \text{ DEET in extraction sample})}{(\mu l \text{ applied})(\text{test composition density})(\% \text{ DEET in test composition})(\text{area extracted})}$$

where:
% DEET in the extraction sample is determined by the gas chromatograph and area extracted =

$$\frac{\pi(c1d1 + c2d2)}{8}$$ where c's and d's are the major and minor diameters, respectively, of the extraction site on the arm.

Test composition density = calculated density of the test composition, % DEET in test composition = theoretical or gc determined % DEET for the test composition, μl applied = amount of DEET test composition applied to each 6×6 cm portion of the 6×12 cm test site.

In this manner, a percent retention after 6 hours can be determined for each test composition and their controls (without acrylate polymers) on each test participant.

LABORATORY MOSQUITO REPELLENCY TEST

A "Standard Test Method(s) for Laboratory Testing of Non-Commercial Mosquito Repellent Formulations on the Skin," ASTM: E951-83, was used to determine the length of time that the formulation provided 95% protection against mosquitoes.

The repellent formulations were applied to the prescribed test sites at a rate of 2 mg of total formulation per square centimeter. These treated sites were subsequently exposed to avid mosquitoes for 90 seconds to determine the number which would feed on the site. The number was recorded for each formulation as well as for an untreated control site. The specific process consisted of transferring fifteen 5-15 day old female Aedes Egypti mosquitoes to the modified small test cages. These were brought into the climatically controlled room ½-¾ hour prior to exposure. At the appropriate time the small test cages were placed on the arm over the treated test sites. One minute later the removable slide was withdrawn to expose the sites to the mosquitoes. The number of feeding mosquitoes at 90 seconds was counted and the cage closed. An untreated control site was run at the same time in the same manner on the thigh. (After each exposure the mosquitoes were sacrificed and fresh ones used for the next exposure.) This entire sequence was repeated each hour until the mosquito repellency fell below 95%. The sites were exposed one more time to verify that the repellency had dropped below 95%.

The compositions of the invention can be prepared as oil-in-water emulsions, water-in-oil emulsions or in solvent.

The oil-in-water emulsions can be prepared in the conventional manner by first formulating the oil and water phases separately and mixing the two together. The oil phase ingredients are heated to about 180° F.

(82° C.) or until the mixture appears clear. The emulsifying agent is then added to the oil phase (or it can be included in the initial mixture if it is lipophilic).

The water phase, which typically consists of water, humectants, thickeners and preservatives, is prepared by heating the ingredients (generally without the thickeners) to about 180° F. (82° C.). The thickeners are then slowly added, with stirring, followed by heating the entire mixture to about 190°-200° F. (88°-93° C.).

The hot water phase is slowly added to the agitating oil phase until inversion occurs. The active agents of the composition may be solid or liquid, but the entire formulation should be somewhat fluid at skin temperatures for ease of application.

The major constituent of the oil phase is the active agent. The oil phase contains about 2 to 70 percent by weight of the acrylate polymer with the preferred range being from about 4 to 50 percent by weight. At levels below 2 percent, the polymer is less effective in holding a significant amount of the active agent on the skin when the skin is exposed to water. At levels above 60 percent, the formulation generally becomes sticky and unpleasant feeling.

For mosquito repellents, the amount of acrylate polymers present will be towards the lower end of the preferred range.

The water phase preferably makes up about 35 to 95 percent by weight of the composition, and preferably 40 to 85 percent.

Any oil-in-water emulsifying agent conventionally used in these formulations may be used in the compositions of the present invention. It has been found, however, that the emulsifier can influence substantivity to some extent. Emulsifiers which provide good substantivity include the 82-mole ethoxylate of glyceryl tallowate, glyceryl stearate, and the 20-mole ethoxylate of cetyl/stearyl alcohol. The emulsifier is preferably present in an amount ranging from about 1 to 10 percent by weight of the composition and preferably, 2 to 4 percent by weight.

Water-in-oil emulsion are generally prepared by heating the oil and water phases, and slowly adding the water phase to the oil phase with good agitation. Homogenization may be helpful, but it is not necessary. The addition of low levels of stabilizing ingredients in the water phase has been shown to be helpful. Salts such as magnesium sulfate have proven to be useful emulsion stabilizers, and they do not significantly affect the water resistance of the formulations. The addition of water soluble gums such as guar derivatives, xanthan gum, and aloe vera and thickeners such as hydroxyl ethyl cellulose, hydroxy methyl cellulose and carboxy vinyl polymers have been found to be helpful in stabilizing the emulsions.

Formulations in solvent can be prepared by simply adding the ingredients to the solvent and mixing.

EXAMPLE 1

This example compares DEET control in solvent vs. DEET with Acrylate Polymers in solvent:

| Composition | Theoretical μl DEET Applied | μl of DEET Extracted (GLC) after 5 Hours | % DEET Recovered | Difference from Control |
|---|---|---|---|---|
| 8.8% Acrylate Polymer* based on DEET (5 g of DEET, 0.44 g Acrylate polymer and 94.56 g of solvent) | 3.22 | 2.16 | 67.1 | +24.5% |
| 5% DEET Control (5 g of DEET, 95 g solvent)** 5% DEET | 4.37 | 1.86 | 42.6 | 0 |

*Acrylate Polymer - 10:90 acrylic acid:isooctyl acrylate (AA:IOA)
**Solvent - isopropyl alcohol

EXAMPLES 2–4

Examples 2–4 compare percent DEET retention versus percent Polymer in Formulation using solvent.

| | | Percent DEET Retention | | |
|---|---|---|---|---|
| Percent Polymer* in DEET** | | Test Formulation | Control*** Formulation | Difference |
| Ex. 2 | 33.3 | 43.5 | 27.0 | +16.5 |
| Ex. 3 | 50 | 41.0 | 20.7 | +20.3 |
| Ex. 4 | 66.7 | 58.5 | 26.1 | +32.4 |

*5:15:85 mole ratio acrylic acid:stearyl methacrylate:isooctyl acrylate polymer (AA:SMA:IOA) prepared at 30% monomer in ethyl acetate
**Contain 6.7% DEET in 1:1 isopropyl alcohol:methylethyl ketone
***Control contains no polymer

EXAMPLES 5–8

The following showed the effect of additives in the formulation. They are formulated as oil-in-water emulsions with 20:80 acrylic acid:isooctyl acrylate polymer.

| | Type | % Deet | Polymer: DEET Ratio | Additive | Treatment | Control | Difference |
|---|---|---|---|---|---|---|---|
| Ex. 5 | O/W Emulsion | 15 | 1:4 | Varonic L148 - PEG82 Glyceryl Monotallowate | 63.6 | 45.7 | +17.9 |
| Ex. 6 | O/W Emulsion | 15 | 1:4 | Pationic SSL - Sodium Stearoyl Lactylate | 67.1 | 51.6 | +15.5 |
| Ex. 7 | O/W Emulsion | 15 | 1:4 | Arosurf TA 100 - Distearyldimonium Chloride | 50.6 | 52.8 | −2.2 |
| Ex. 8 | O/W Emulsion | 15 | 1:4 | Carbopol Thickener 934 | 54.0 | 46.3 / 49.0 ± 6.8 | +7.7 |

EXAMPLES 9–11

The following examples demonstrate mosquito repellency under various climatic conditions. The formulations are as follows:

| Formulation A 20% DEET Oil-in-Water Emulsion | |
|---|---|
| | W/W % |
| Deionized Water | 63.46 |
| Veegum Magnesium Aluminum Silicate | 0.59 |
| Natrosol 250HR Hydroxyethyl Cellulose | 0.39 |
| Lexemul AS Glyceryl monostearate | 1.16 |
| Polymer, 7.5:7.5:85 AA:SMA:IOA (1 to 3 by weight in DEET) | 13.32 |
| DEET | 10.01 |
| Arlamol E PPG-15 Stearyl Ether | 0.53 |
| Waxenol 816 Cetyl Stearyl Ether | 0.59 |
| Unimate 600 Dicapryl Adipate | 5.83 |
| Promulgen G Stearyl Alcohol (and) Ceteareth-20 | 3.88 |
| Diazolidinyl:Urea:Methyl Paraben: Propyl Paraben:Propylene Propylene Glycol (Germaben II) | 0.24 |

| Formulation B 30% DEET Oil-in-Water Emulsion | |
|---|---|
| | W/W % |
| Deionized Water | 43.19 |
| Carbowax 400 Polyethylene Glycol | 2.00 |
| Liponic EG-7 Glycereth-7 | 2.00 |
| Veegum Magnesium Aluminum Silicate | 0.88 |
| Natrosol 250HR Hydroxyethyl Cellulose | 0.88 |
| Varonic LI420 PEG-200 Glyceryl Monotallowate | 1.00 |
| Varonic LI48 PEG-82 Glyceryl Monotallowate | 2.40 |
| Lexemul AS Glyceryl Monostearate | 2.40 |
| Polymer, 7.5:7.5:85 AA:SMA:IOA (1 to 3 by weight in DEET) | 20.00 |
| DEET | 15.00 |
| Lexol PG865 Propylene Glycol Dicaprylate/Dicaprate | 6.00 |
| Arlamol E PPG-15 Stearyl Ether | 1.60 |
| Adol 63 Cetyl Stearyl Ether | 1.60 |
| Waxenol 816 Cetyl Palmitate | 0.80 |
| Germaben II | 0.25 |

| Formulation C 50% DEET Water-in-Oil Emulsion | |
|---|---|
| | W/W % |
| Polymer, 7.5:7.5:85 AA:SMA:IOA (1 to 3 by weight in DEET) | 16.67 |
| DEET | 38.50 |
| Dicapryl Adipate | 9.00 |
| Witcamide 70 Stearamide MEA | 4.00 |
| Adol-63 Cetyl Stearyl Ether | 2.40 |
| Cabosil M-5 Fumed Silicon Dioxide | 1.20 |
| Orgasol - 2002 Polyamide type 12 | 1.60 |
| Water | 24.63 |
| Carbowax 400 | 2.00 |

| Formulation D 20% DEET Oil-In Water Emulsion - Positive Control | |
|---|---|
| | W/W % |
| Veegum Magnesium Aluminum Silicate | 0.59 |
| Natrosol 250HR Hydroxyethyl Cellulose | 0.39 |
| Lexemul AS Glyceryl Monostearate | 1.16 |
| DEET | 20.00 |
| Arlamol E PPG-15 Stearyl Ether | 0.53 |
| Waxenol 816 Cetyl Palmitate | 0.59 |
| Unimate 600 Dicapryl Adipate | 5.83 |
| Promulgen G Stearyl Alcohol (and) Ceteareth-20 | 3.88 |
| Germaben II | 0.24 |
| Deionized Water | QS to 100 |

| Formulation E 30% DEET Oil-in-Water Emulsion - Positive Control | |
|---|---|
| | W/W % |
| Carbowax 400 Polyethylene Glycol | 2.00 |
| Liponic EG-7 Glycereth-7 | 2.00 |
| Veegum Magnesium Aluminum Silicate | 0.88 |
| Natrosol 250HR Hydroxyethyl Cellulose | 0.88 |
| Varonic LI420 PEG-200 Glyceryl Monotallowate | 1.00 |
| Varonic LI48 PEG-82 Glyceryl Monotallowate | 2.40 |
| Lexemul AS Glyceryl Monostearate | 2.40 |
| DEET | 30.00 |
| Lexol PG865 Propylene Glycol Dicaprylate/Dicaprate | 6.00 |
| Arlamol E PPG-15 Stearyl Ether | 1.60 |
| Adol 63 Cetyl Stearyl Ether | 1.60 |
| Waxenol 816 Cetyl Palmitate | 0.80 |
| Germaben II | 0.25 |
| Deionized Water | QS to 100 |

Mosquito Repelling Test[1]

EXAMPLE 9

| 1. Climate: Hot–Low Humidity[2] | | | | | |
|---|---|---|---|---|---|
| | | Percent Repellency[3], Hours after Treatment | | | |
| Formulations | | 11 | 13 | 15 | 16 |
| A | 20% DEET | 99 | 96 | 97 | 93 |
| D | 20% DEET control[4] | 83 | 28 | 30 | 14 |
| B | 30% DEET | 100 | 100 | 100 | 100 |
| E | 30% DEET control[4] | 81 | 99 | 98 | 90 |
| C | 50% DEET | 100 | 100 | 97 | 100 |

[1]Modified ASTM E 951-83
[2]86–110° F., 14–44% RH
[3]10 replications, equals $\frac{\text{control bites} - \text{treatment bites}}{\text{control bites}} \times 100$
[4]Repellent control without acrylate polymer

EXAMPLE 10

| 2. Climate: Variable High Humidity[5] | | | | | |
|---|---|---|---|---|---|
| | Percent Repelling, Hours after Treatment | | | | |
| Formulations | 9 | 11 | 12 | 14 | 16 |
| A | 92 | 93 | 87 | 88 | 63 |
| D | 82 | 86 | 37 | 65 | 77 |
| B | 99 | 98 | 98 | 85 | 83 |
| E | 74 | 72 | 77 | 0 | 67 |
| C | 100 | 100 | 96 | 100 | 93 |

[5]78–95° F., 74–100% RH

EXAMPLE 11

| 3. Climate: Constant High Humidity[6] | | | | | |
|---|---|---|---|---|---|
| | Percent Repelling, Hours after Treatment | | | | |
| Formulations | 9 | 11 | 12 | 14 | 16 |
| A | 95 | 89 | 93 | 99 | 89 |
| D | 100 | 100 | 89 | 100 | 89 |
| B | 100 | 100 | 96 | 100 | 100 |

3. Climate: Constant High Humidity[6]

| Formulations | Percent Repelling, Hours after Treatment | | | | |
|---|---|---|---|---|---|
| | 9 | 11 | 12 | 14 | 16 |
| E | 97 | 93 | 99 | 96 | 86 |
| C | 100 | 100 | 96 | 100 | 100 |

[6] 75° F., 95-100% RH

EXAMPLE 12

Mosquito repellency tests conducted under variable high humidity with different DEET amounts and varied formulations:

| Formulation F | |
|---|---|
| Deionized Water | 43.57 |
| Polyethylene Glycol | 1.30 |
| Glycereth-7 | 1.94 |
| Magnesium Aluminum Silicate | .70 |
| Hydroxyethyl Cellulose | .70 |
| PEG-82 Glyceryl Monotallowate | 1.03 |
| Glyceryl Monostearate | 3.48 |
| Polymer (85:7.5:7.5 Mole Ratio Iso-octyl Acrylate:Stearyl Methacrylate:Acylic Acid) | 5.83 |
| DEET | 35.00 |
| Propylene Glycol Dicaprylate/Dicaprate | 3.22 |
| PPG-15 Stearyl Ether | .86 |
| Cetyl-Stearyl Ether | .86 |
| Cetyl Palmitate | .65 |
| PEG-200 Glyceryl Monotallowate | .65 |
| Diazolidinyl:Urea:Methyl Paraben:Propyl Paraben:Propylene Glycol | .24 |

| Formulation G | |
|---|---|
| Deionized Water | 42.38 |
| Polyethylene Glycol | 1.94 |
| Glycereth-7 | 1.94 |
| Magnesium Aluminum Silicate | .70 |
| Hydroxyethyl Cellulose | .70 |
| PEG-82 Glyceryl Monotallowate | 1.55 |
| Glyceryl Monostearate | 3.48 |
| Polymer (85:7.5:7.5 Mole Ratio Iso-octyl Acrylate:Stearyl Methacrylate:Acylic Acid) | 5.83 |
| DEET | 35.00 |
| Propylene Glycol Dicaprylate/Dicaprate | 3.22 |
| PPG-15 Stearyl Ether | .86 |
| Cetyl-Stearyl Ether | .86 |
| Cetyl Palmitate | .65 |
| PEG-200 Glyceryl Monotallowate | .65 |
| Diazolidinyl:Urea:Methyl Paraben:Propyl Paraben:Propylene Glycol | .24 |

| Formulation H | |
|---|---|
| Deionized Water | 44.40 |
| Polyethylene Glycol | 1.30 |
| Glycereth-7 | 1.94 |
| Magnesium Aluminum Silicate | .70 |
| Hydroxyethyl Cellulose | .70 |
| PEG-82 Glyceryl Monotallowate | 1.55 |
| Glyceryl Monostearate | 2.32 |
| Polymer (85:7.5:7.5 Mole Ratio Iso-octyl Acrylate:Stearyl Methacrylate:Acylic Acid) | 5.83 |
| DEET | 35.00 |
| Propylene Glycol Dicaprylate/Dicaprate | 3.22 |
| PPG-15 Stearyl Ether | .86 |
| Cetyl-Stearyl Ether | .86 |
| Cetyl Palmitate | .65 |
| PEG-200 Glyceryl Monotallowate | .43 |
| Diazolidinyl:Urea:Methyl Paraben:Propyl Paraben:Propylene Glycol | .24 |

| Formulation I | |
|---|---|
| Deionized Water | 45.34 |
| Polyethylene Glycol | 1.30 |
| Glycereth-7 | 1.30 |
| Magnesium Aluminum Silicate | .70 |
| Hydroxyethyl Cellulose | .70 |
| PEG-82 Glyceryl Monotallowate | 1.03 |
| Glyceryl Monostearate | 2.32 |
| Polymer (85:7.5:7.5 Mole Ratio Iso-octyl Acrylate:Stearyl Methacrylate:Acylic Acid) | 5.83 |
| DEET | 35.00 |
| Propylene Glycol Dicaprylate/Dicaprate | 3.22 |
| PPG-15 Stearyl Ether | .86 |
| Cetyl-Stearyl Ether | .86 |
| Cetyl Palmitate | .65 |
| PEG-200 Glyceryl Monotallowate | .65 |
| Diazolidinyl:Urea:Methyl Paraben:Propyl Paraben:Propylene Glycol | .24 |

| Formulation J | |
|---|---|
| Deionized Water | 43.19 |
| Polyethylene Glycol | 2.00 |
| Glycereth-7 | 2.00 |
| Magnesium Aluminum Silicate | .88 |
| Hydroxyethyl Cellulose | .88 |
| PEG-82 Glyceryl Monotallowate | 2.40 |
| Glyceryl Monostearate | 2.40 |
| Polymer (85:7.5:7.5 Mole Ratio Iso-octyl Acrylate:Stearyl Methacrylate:Acylic Acid) | 5.00 |
| DEET | 30.00 |
| Propylene Glycol Dicaprylate/Dicaprate | 6.00 |
| PPG-15 Stearyl Ether | 1.60 |
| Cetyl-Stearyl Ether | 1.60 |
| Cetyl Palmitate | .80 |
| PEG-200 Glyceryl Monotallowate | 1.00 |
| Diazolidinyl:Urea:Methyl Paraben:Propyl Paraben:Propylene Glycol | .25 |

| Formulation K | |
|---|---|
| Deionized Water | 51.12 |
| Polyethylene Glycol | 1.16 |
| Glycereth-7 | 1.16 |
| Magnesium Aluminum Silicate | .75 |
| Hydroxyethyl Cellulose | .75 |
| PEG-82 Glyceryl Monotallowate | 1.38 |
| Glyceryl Monostearate | 2.08 |
| Polymer (85:7.5:7.5 Mole Ratio Iso-octyl Acrylate:Stearyl Methacrylate:Acylic Acid) | 5.00 |
| DEET | 30.00 |
| Propylene Glycol Dicaprylate/Dicaprate | 3.46 |
| PPG-15 Stearyl Ether | .93 |
| Cetyl-Stearyl Ether | .93 |
| Cetyl Palmitate | .46 |
| PEG-200 Glyceryl Monotallowate | .51 |
| Diazolidinyl:Urea:Methyl Paraben:Propyl Paraben:Propylene Glycol | .24 |

EXAMPLE 12

| | Mosquito Repellency Test[1] Climate: Variable High Humidity[2] | | | | | | |
|---|---|---|---|---|---|---|---|
| | Percent Repelling[3], Hours After Application | | | | | | |
| Formulation | 8 | 10 | 12 | 13 | 14 | 15 | 16 |
| F | 100 | 100 | 100 | 100 | 100 | 94 | 100 |
| G | 98 | 97 | 94 | 100 | 95 | 94 | 100 |
| H | 98 | 100 | 96 | 100 | 95 | 100 | 100 |
| I | 100 | 100 | 98 | 100 | 97 | 100 | 100 |
| J | 100 | 100 | 94 | 96 | 90 | 94 | 100 |
| K | 98 | 100 | 92 | 96 | 85 | 85 | 100 |

[1] Via modified ASTM:E-951-83 15, 5-15 day old, female Aedes Egypti mosquitoes
[2] 80-100-80° F., 100-75-100% relative humidity
[3] Repellency = total control bites − $\frac{\text{total test formulation bites}}{\text{total control bites}} \times 100$ While the active agent of the present invention has been described herein as DEET, it is expected that other insect repellents such as 2,5-dimethyl-2,5-hexanediol, dimethylphthalate, dibutylphthalate, ethylhexanediol, indalene, pyrethrins and naphthalene could provide equally useful mosquito repellent compositions when combined with the oil soluble, water insoluble acrylate polymers as taught herein.

Similarly, although the compositions of the present invention have been described as mosquito repellents, it will be appreciated that they will be equally effective against those insects which are repelled by the active agent. For example, DEET is recognized to be an effective repellent for biting flies, chiggers, deer flies, fleas, stable flies and terrestrial leeches as well as for mosquitoes.

What is claimed is:

1. A mosquito repellent composition comprising:
   an effective amount of a mosquito repellent;
   at least 2 percent by weight based on said active agent of an oil soluble, water insoluble acrylate polymer having a solubility parameter of 6 to 10 (cal./cc.)$^{\frac{1}{2}}$ in poorly hydrogen bonding solvents and a Brookfield viscosity between about 50 and 250,000 cps. when measured at 25 percent nonvolatiles; and
   a liquid carrier.

2. The composition according to claim 1 wherein said polymer is derived from the polymerization of the same or different ester monomers of the formula:

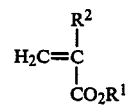

wherein $R^1$ is an alkyl radical containing 4 to 18 carbon atoms in cyclic, straight or branched chain configuration, $R^2$ is hydrogen or lower alkyl; and up to 30 mole percent of the same or different acid monomers of the formula:

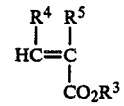

wherein $R^3$ is H or an alkyl group containing 1 to 18 carbon atoms; $R^4$ is hydrogen, methyl, or $-CO_2R^3$, and $R^5$ is hydrogen, lower alkyl or $-CH_2CO_2R^3$; provided when $R^4$ is not hydrogen, $R^5$ is hydrogen and when $R^5$ is not hydrogen, $R^4$ is hydrogen.

3. The composition of claim 2 wherein said polymer contains from 100 to 80 mole percent of said ester monomers and from 0 to 20 mole percent of said acid monomers.

4. The composition of claim 2 wherein said ester monomer is an alkyl ester of acrylic acid or methacrylic acid.

5. The composition of claim 4 wherein said mosquito repellant is DEET.

6. The composition of claim 1 wherein said polymer is a terpolymer of iso-octyl acrylate, stearyl methacrylate, and acrylic acid.

7. The composition of claim 6 wherein said polymer contains 85 mole percent iso-octyl acrylate, 7.5 mole percent stearyl methacrylate and 7.5 mole percent of acrylic acid.

8. The composition of claim 7 containing 4 to 50 percent based on DEET by weight of said polymer.

9. The composition of claim 1 wherein said polymer is a copolymer of isooctyl acrylate and acrylic acid.

* * * * *

UNITED STATES PATENT AND TRADEMARK OFFICE
CERTIFICATE OF CORRECTION

PATENT NO. : 4,816,256

DATED : March 28, 1989

INVENTOR(S) : Neil A. Randen

It is certified that error appears in the above-identified patent and that said Letters Patent is hereby corrected as shown below:

Col. 3, line 58, "novolatiles" should read --nonvolatiles--.

Col. 5, line 32, "identation" should read --indentation--.

Col. 7, line 65, "hydroxyl" should reach --hydroxy--.

Col. 11, line 25, "Methacrylate:Acylic" should read --Methacrylate:Acrylic--.

Col. 11, line 45, "Methacrylate:Acylic" should read --Methacrylate:Acrylic--.

Col. 11, line 65, "Methacrylate:Acylic" should read --Methacrylate:Acrylic--.

Col. 12, line 20, "Methacrylate:Acylic" should read --Methacrylate:Acrylic--.

Col. 12, line 40, "Methacrylate:Acylic" should read --Methacrylate:Acrylic--.

UNITED STATES PATENT AND TRADEMARK OFFICE
CERTIFICATE OF CORRECTION

PATENT NO. : 4,816,256

DATED : March 28, 1989

INVENTOR(S) : Neil A. Randen

It is certified that error appears in the above-identified patent and that said Letters Patent is hereby corrected as shown below:

Col. 12, line 60, "Methacrylate:Acylic" should read
--Methacrylate:Acrylic--.

Signed and Sealed this

Ninth Day of January, 1990

Attest:

JEFFREY M. SAMUELS

*Attesting Officer*     *Acting Commissioner of Patents and Trademarks*